(12) United States Patent
May et al.

(10) Patent No.: US 12,374,450 B2
(45) Date of Patent: Jul. 29, 2025

(54) APPLIED USAGE COUNT READER AND DISPLAY DEVICE THAT DETERMINES A NUMBER OF APPLIED USES REMAINING FOR A LIMITED-USE MEDICAL DEVICE OR INSTRUMENT USED BY A SURGICAL OR ROBOTIC SYSTEM

(71) Applicants: Kevin Brent May, Henderson, NV (US); Clifton E Parker, Panama City Beach, FL (US)

(72) Inventors: Kevin Brent May, Henderson, NV (US); Clifton E Parker, Panama City Beach, FL (US)

(73) Assignee: RESTORE ROBOTICS REPAIRS LLC, Panama City Beach, FL (US)

( * ) Notice: Subject to any disclaimer, the term of this patent is extended or adjusted under 35 U.S.C. 154(b) by 0 days.

(21) Appl. No.: 18/665,571

(22) Filed: May 16, 2024

(65) Prior Publication Data
US 2024/0296944 A1    Sep. 5, 2024

Related U.S. Application Data

(63) Continuation of application No. 17/724,276, filed on Apr. 19, 2022, now Pat. No. 12,009,096.

(60) Provisional application No. 63/176,730, filed on Apr. 19, 2021.

(51) Int. Cl.
*G16H 40/40* (2018.01)
*A61B 90/90* (2016.01)

(52) U.S. Cl.
CPC .......... *G16H 40/40* (2018.01); *A61B 90/90* (2016.02)

(58) Field of Classification Search
CPC ........ G16H 40/40; G16H 40/20; G16H 40/63; G16H 20/40; A61B 90/90; A61B 2017/00477; A61B 34/30; A61B 90/98; A61B 2090/0803
See application file for complete search history.

(56) References Cited

U.S. PATENT DOCUMENTS

| | | | | |
|---|---|---|---|---|
| 8,308,355 | B2 * | 11/2012 | Lane | G07C 3/08 374/170 |
| 11,495,003 | B1 * | 11/2022 | Agarwal | G06Q 30/0643 |
| 11,633,531 | B2 * | 4/2023 | Fung | G08B 21/182 340/540 |
| 2002/0193709 | A1 * | 12/2002 | Bolze | A61B 17/22029 601/4 |
| 2003/0002562 | A1 * | 1/2003 | Yerlikaya | G01K 13/20 374/E13.002 |
| 2006/0276850 | A1 * | 12/2006 | Deffeyes | G01R 33/04 607/27 |

(Continued)

*Primary Examiner* — Nay Tun
(74) *Attorney, Agent, or Firm* — Plager Schack LLP; Mark H. Plager; Stephen Hallberg

(57) ABSTRACT

An applied usage count reader and display device is disclosed. The applied usage count reader and display device is configured to read information embedded in memory of a limited-use medical device used by a surgical or robotic system and determine a remaining number of uses available for the limited-use medical device. The applied usage count reader and display device removes the human element from the determination of useful life left on the limited-use medical device by allowing staff or other authorized users to test the useful life and read the memory on the device at any time when away from the surgical system or operating room.

12 Claims, 7 Drawing Sheets

(56) References Cited

U.S. PATENT DOCUMENTS

| | | | |
|---|---|---|---|
| 2007/0125392 A1* | 6/2007 | Olson, Jr. | A61B 90/90 |
| | | | 128/899 |
| 2008/0114289 A1* | 5/2008 | Muri | A61M 3/0201 |
| | | | 604/294 |
| 2012/0109798 A1* | 5/2012 | Shelton | B60L 53/62 |
| | | | 705/30 |
| 2013/0311314 A1* | 11/2013 | Fernando | G06K 7/10386 |
| | | | 705/17 |
| 2013/0331790 A1* | 12/2013 | Brown | H01R 13/5224 |
| | | | 604/151 |
| 2016/0249919 A1* | 9/2016 | Savage | H01M 10/613 |
| | | | 227/175.1 |
| 2017/0312044 A1* | 11/2017 | Conlon | A61B 17/295 |
| 2018/0286510 A1* | 10/2018 | Kwan | G06Q 30/0633 |
| 2019/0298474 A1* | 10/2019 | Fung | A61F 9/007 |

* cited by examiner

APPLIED USAGE COUNT READER AND DISPLAY DEVICE THAT DETERMINES A NUMBER OF APPLIED USES REMAINING FOR A LIMITED-USE MEDICAL DEVICE OR INSTRUMENT USED BY A SURGICAL OR ROBOTIC SYSTEM

CLAIM OF BENEFIT TO PRIOR APPLICATIONS

This application is a continuation of and claims benefit to U.S. Non-Provisional patent application Ser. No. 17/724,276, entitled "AN APPLIED USAGE COUNT READER AND DISPLAY DEVICE THAT DETERMINES A NUMBER OF APPLIED USES REMAINING FOR A LIMITED-USE MEDICAL DEVICE OR INSTRUMENT USED BY A SURGICAL OR ROBOTIC SYSTEM," filed Apr. 19, 2022. The U.S. Non-Provisional patent application Ser. No. 17/724,276 is incorporated herein by reference.

BACKGROUND

Embodiments of the invention described in this specification relate generally to medical information systems, and more particularly, to an applied usage count reader and display device that determines a number of applied uses remaining for a limited-use medical device or instrument used by a surgical or robotic system.

Some medical devices and surgical instruments are configured for use in a robotic surgical system, such as a "da Vinci Robotic System". When such a medical device or surgical instrument is disconnected from the robotic surgical system, it is not possible for a person to determine key information about the medical device or surgical instrument (hereinafter referred to as a "limited-use medical tool" or "instrument" or "device", a "robotic tool" or "instrument" or "device", a "medical tool" or "instrument" or "device", and/or simply a "tool" or an "instrument" or a "device"). For instance, some of the key information about the robotic instrument may be embedded in memory within the robotic instrument and, therefore, is not human readable. The information embedded in memory of a limited-use robotic instrument includes the number of uses (also known as the "number of useful lives" or the remaining "life" or "available uses") until the robotic instrument is rendered non-functional, as well as the make, model number, serial number, version number, internal specification, or other pertinent data left on the limited-use medical tool.

The number of useful lives on the limited-use medical tool can only be determined when the limited-use medical tool is connected to the very expensive robotic surgical system located in the operating room. As a result, hospital staff is left with ad hoc measures, such as physically marking the number of available uses of the limited-use medical tool left, or the number of completed uses of the limited-use medical tool. However, this ad hoc marking system is prone to human error, which can have severe consequences when incorrect markings result in an expired limited-use medical tool being made available for use in an operating room. Also, physically marking the remaining or completed uses is typically done on the surface of the limited-use medical tool with a pen or other marking process. Such surface markings are prone to fading during cleaning/sterilization of the limited-use medical tool.

Therefore, what is needed is a way to remove the human element from the determination of useful life left on the limited-use medical tool and to allow staff to test the useful life and memory on the limited-use medical tool at any time, and at nearly any location, without the need to use the robotic surgical system or even without needing to be nearby the operating room, as well as to obtain other information stored internally on the limited-use medical tool.

BRIEF DESCRIPTION

A novel applied usage count reader and display device is disclosed. In some embodiments, the applied usage count reader and display device is configured to determine a number of applied uses remaining for a limited-use medical device or instrument used by a surgical or robotic system. In some embodiments, the applied usage count reader and display device reads internally stored data, including the number of applied uses remaining and other pertinent data about the limited-use medical device, as retrieved from the limited-use medical device/instrument without need of the surgical/robotic system. In some embodiments, the internally stored data read by the applied usage count reader and display device comprises data specifying the number of applied uses remaining. In some embodiments, the internally stored data further comprises data specifying a make, a model number, a serial number, a version number, an internal specification, and/or other pertinent data about the limited-use medical tool. In some embodiments, the applied usage count reader and display device is configured for use in writing and/or reprogramming data. In some embodiments, the applied usage count reader and display device is configured for resetting the number of applied uses remaining.

In some embodiments, the applied usage count reader and display device is a hand-held device. In some embodiments, the applied usage count reader and display device is a portable device. In some embodiments, the applied usage count reader and display device is a mobile device. In some embodiments, the applied usage count reader and display device is an integrated device (integrated with other hardware). In some embodiments, the applied usage count reader and display device is powered by batteries. In some embodiments, the applied usage count reader and display device is powered by AC power. In some embodiments, the applied usage count reader and display device is powered by a non-battery DC power source or other power source.

In some embodiments, the applied usage count reader and display device is a first applied usage count reader and display device that is configured to read internally stored data to determine a number of applied uses remaining for a first type of instrument used in connection with a robotic surgical system. In some embodiments, the first applied usage count reader and display device comprises a plurality of surface contacts of a contact printed circuit board (PCB) assembly. In some embodiments, the first type of instrument includes a plurality of pogo pins which, when aligned with and connected to the plurality of surface contacts of the contact PCB, enable the first applied usage count reader and display device to retrieve and decode data for the number of applied uses remaining, and the other internally stored data as needed, from an EEPROM memory unit embedded in the first type of instrument and then display the number of applied uses remaining and other information from the internally stored data as needed.

In some embodiments, the applied usage count reader and display device is a second applied usage count reader and display device that is configured to read internally stored data to determine a number of applied uses remaining for a second type of instrument used in connection with a robotic surgical system. In some embodiments, the second type of instrument includes a magnet that is detected by the second applied usage count reader and display device which triggers a radio signal to energize an RFID tag of the second type of instrument and send data for the number of applied uses remaining, and the other internally stored data as needed, from the second type of instrument to an RFID active reader and antenna of the second applied usage count reader and display device, which decodes the data and displays the number of applied uses remaining and other information from the internally stored data as needed.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Figure 1:
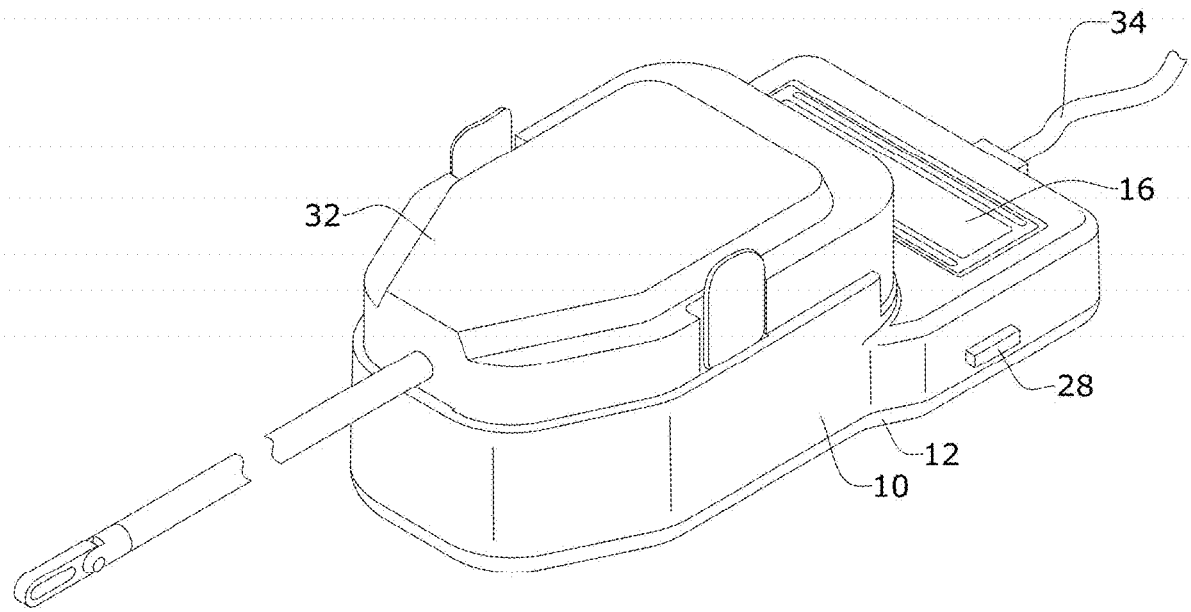

Having thus described the invention in general terms, reference is now made to the accompanying drawings, which are not necessarily drawn to scale, and which show different views of different example embodiments, and wherein:

FIG. 1 conceptually illustrates a perspective view of a limited-use robotic instrument engaged with a first applied usage count reader and display device in some embodiments.

Figure 2:
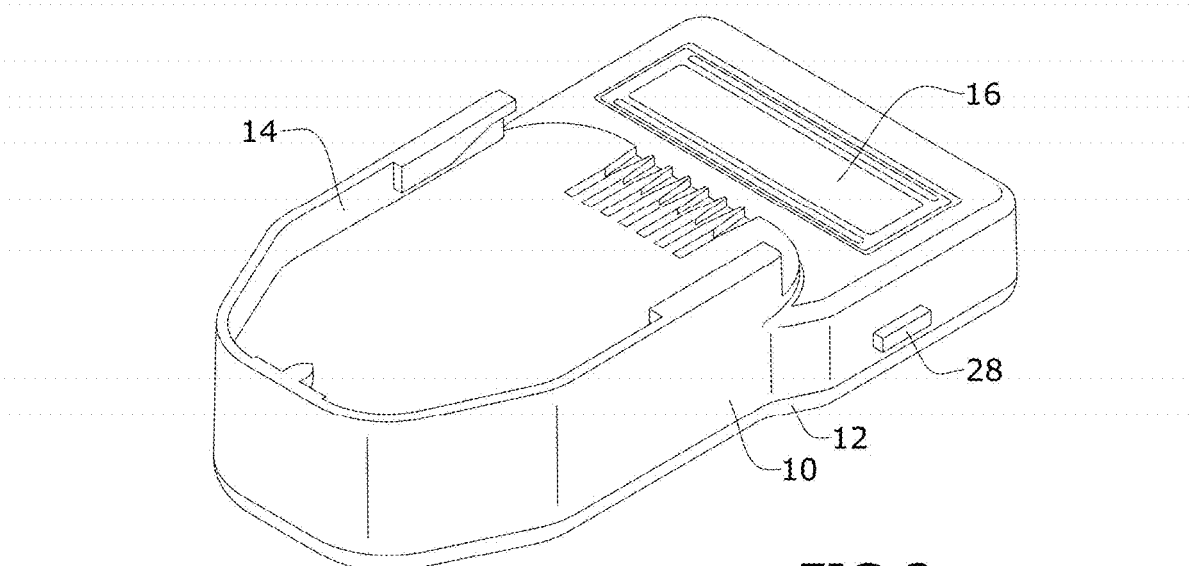

FIG. 2 conceptually illustrates a perspective view of the first applied usage count reader and display device of FIG. 1.

Figure 3:
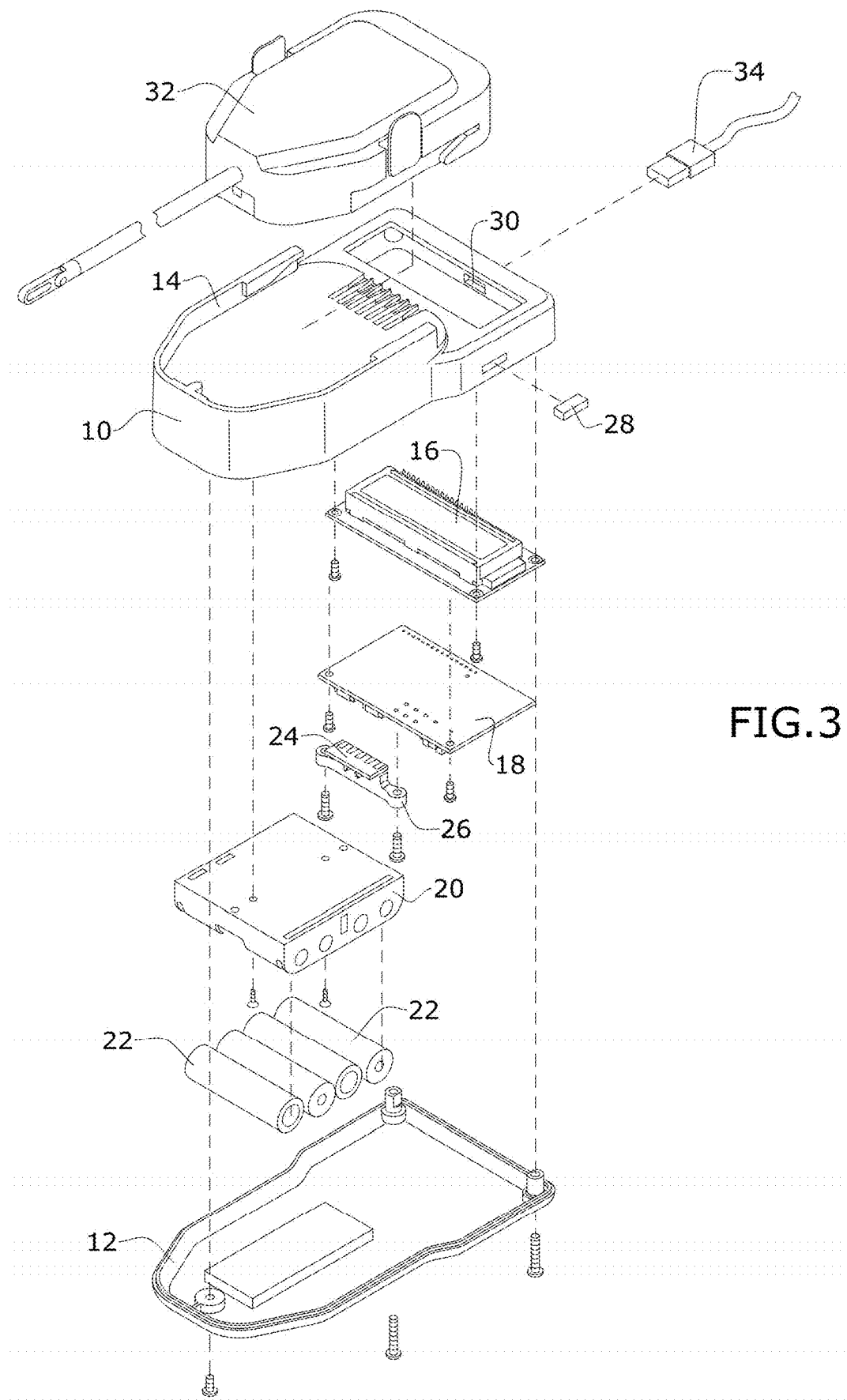

FIG. 3 conceptually illustrates an exploded view of the first applied usage count reader and display device in some embodiments.

Figures 4, 5:
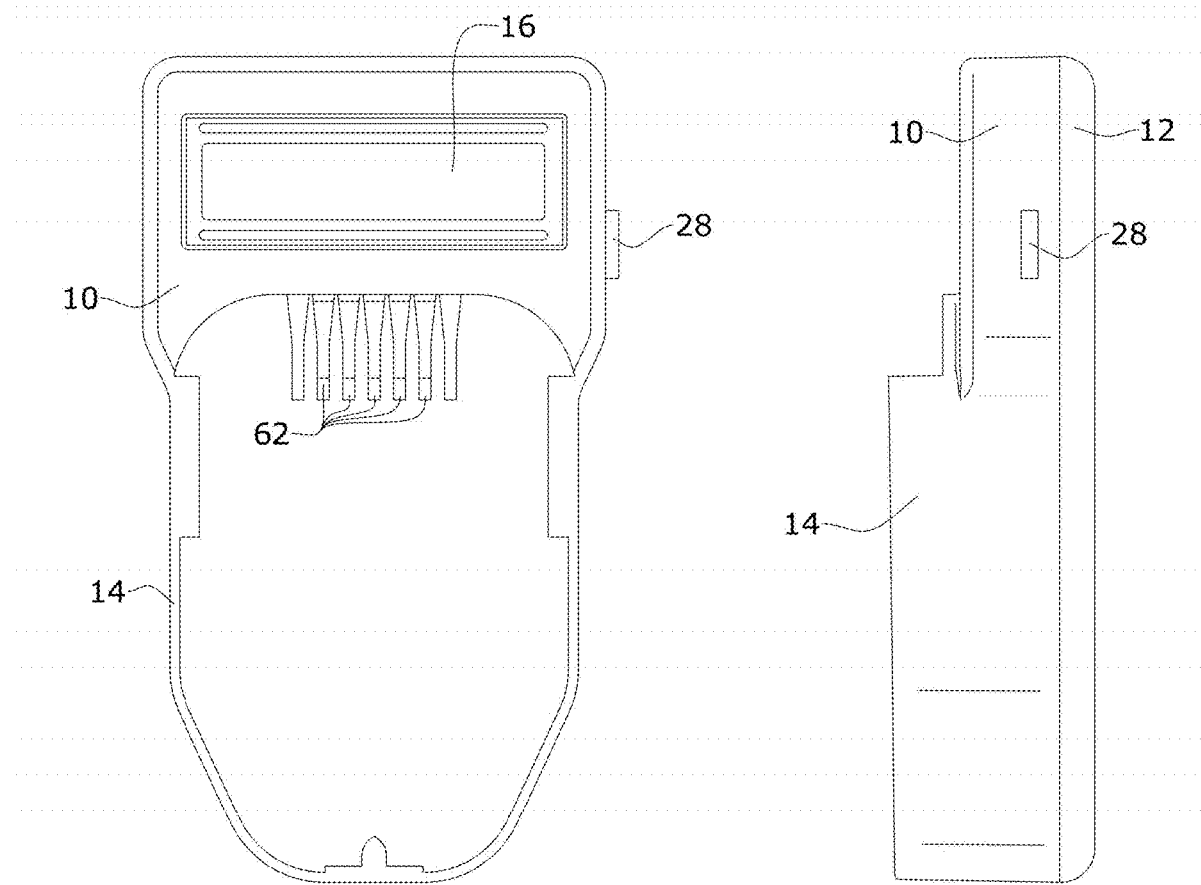

FIG. 4 conceptually illustrates a top view of the first applied usage count reader and display device in some embodiments.

FIG. 5 conceptually illustrates a side view of the first applied usage count reader and display device in some embodiments.

Figures 6, 7:
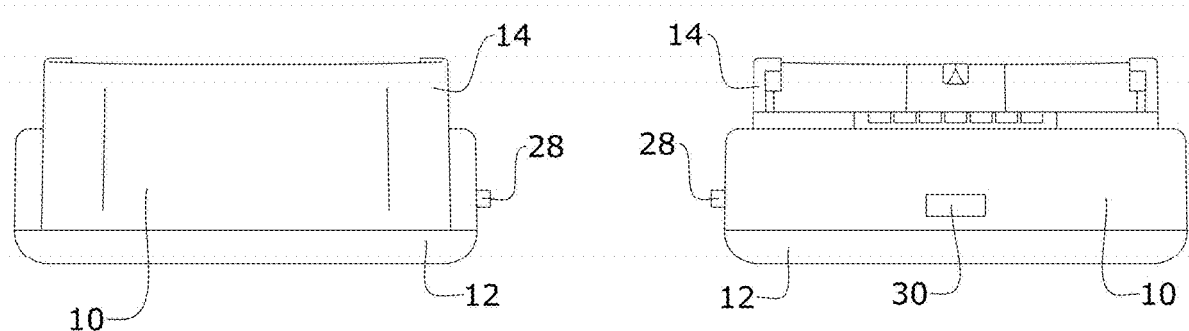

FIG. 6 conceptually illustrates a front view of the first applied usage count reader and display device in some embodiments.

FIG. 7 conceptually illustrates a rear view of the first applied usage count reader and display device in some embodiments.

Figure 8:
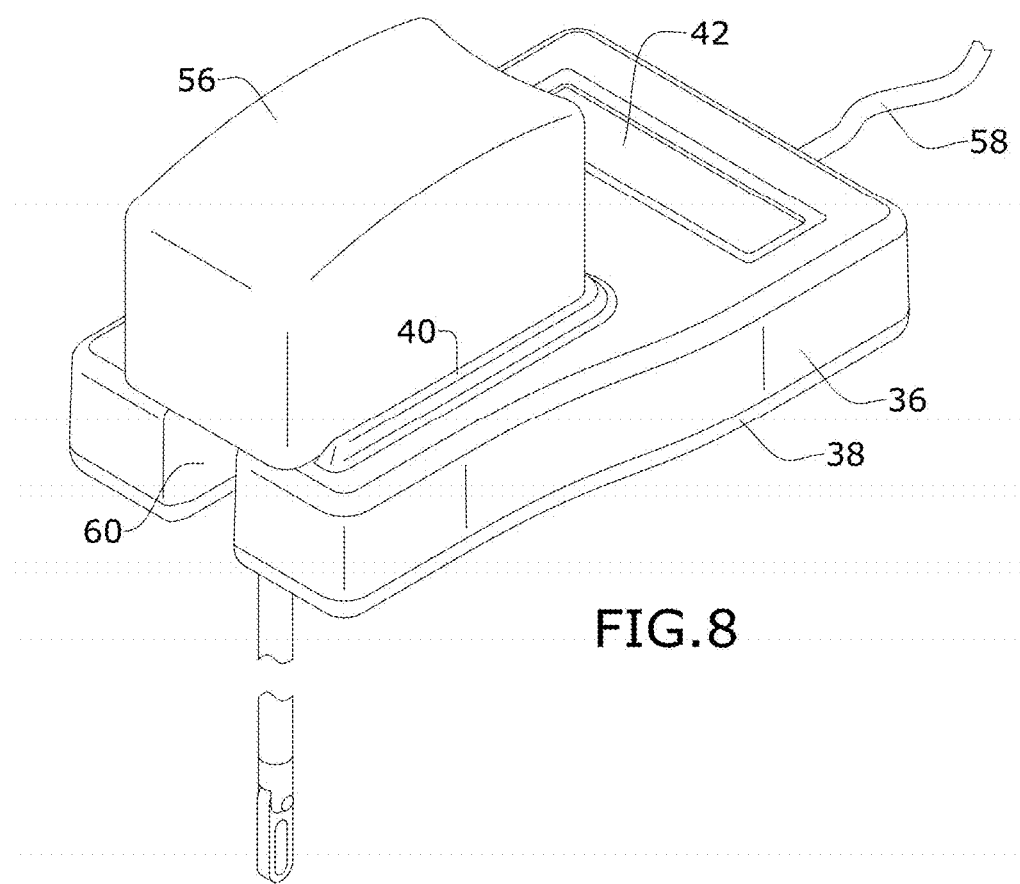

FIG. 8 conceptually illustrates a perspective view of a limited-use robotic instrument engaged with a second applied usage count reader and display device in some embodiments.

Figure 9:
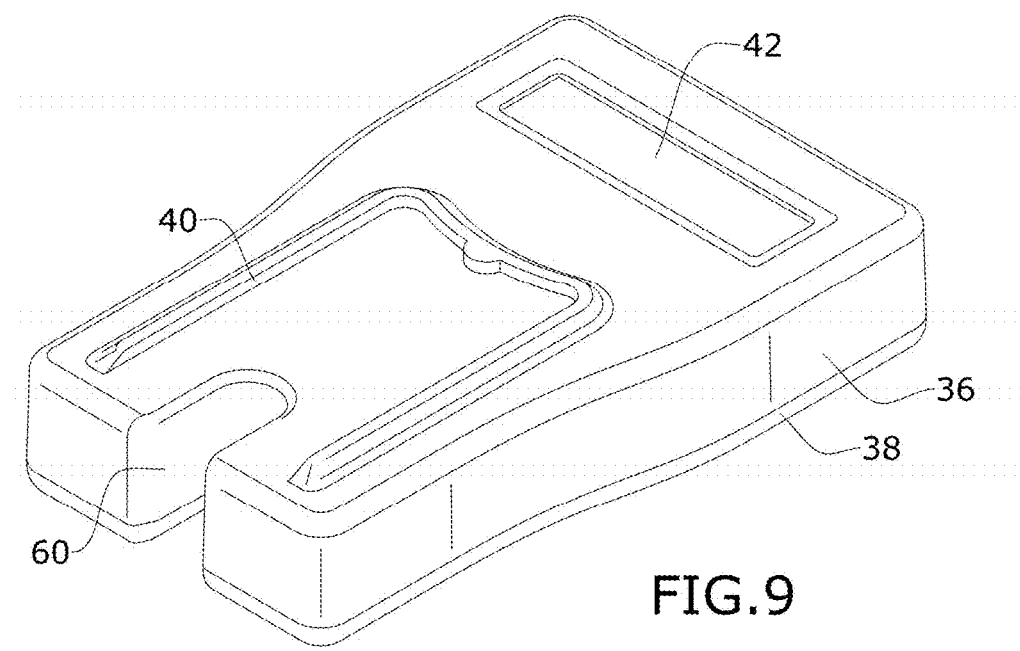

FIG. 9 conceptually illustrates a perspective view of the second applied usage count reader and display device of FIG. 8.

Figure 10:
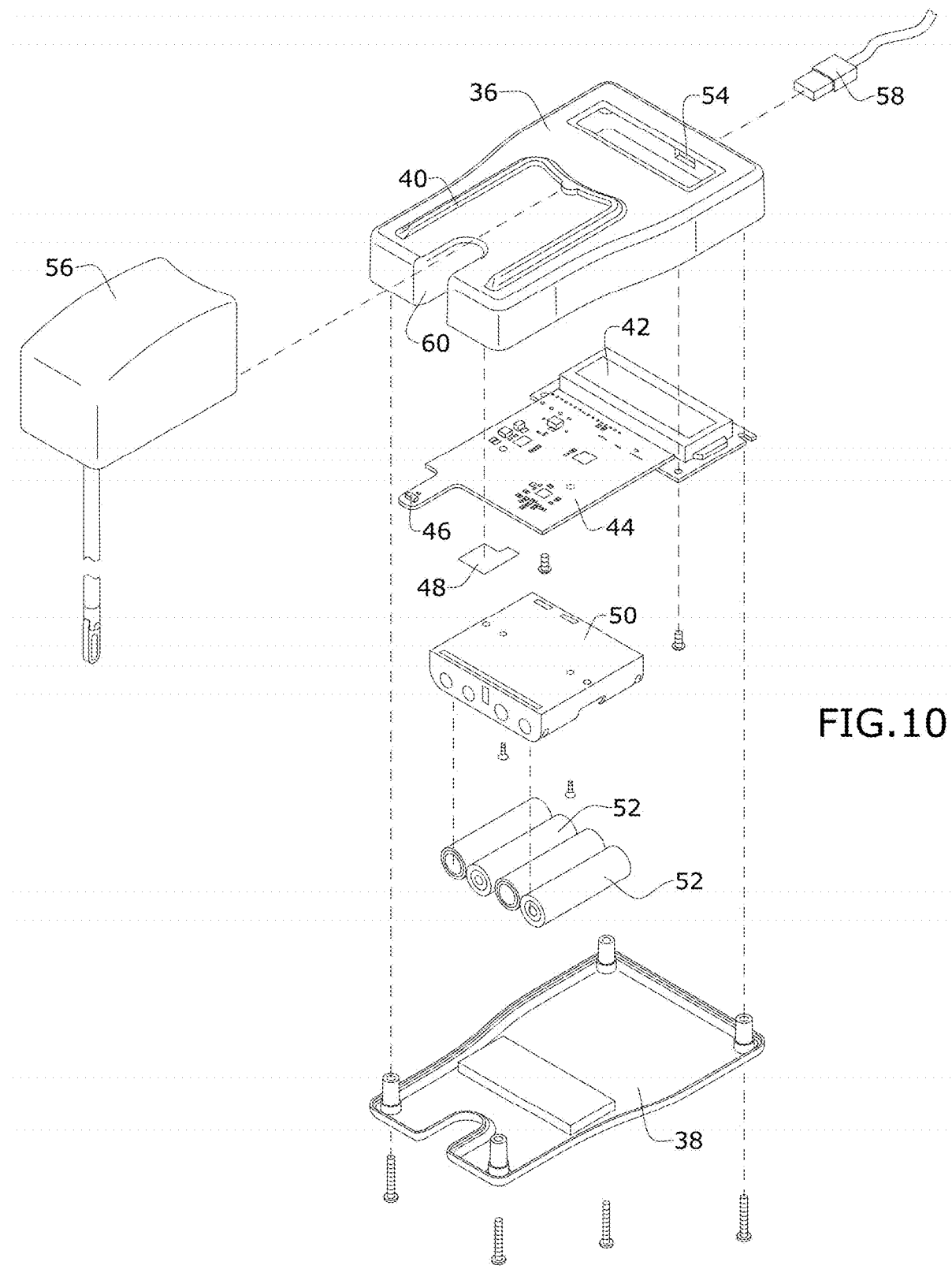

FIG. 10 conceptually illustrates an exploded view of the second applied usage count reader and display device in some embodiments.

Figures 11, 12:
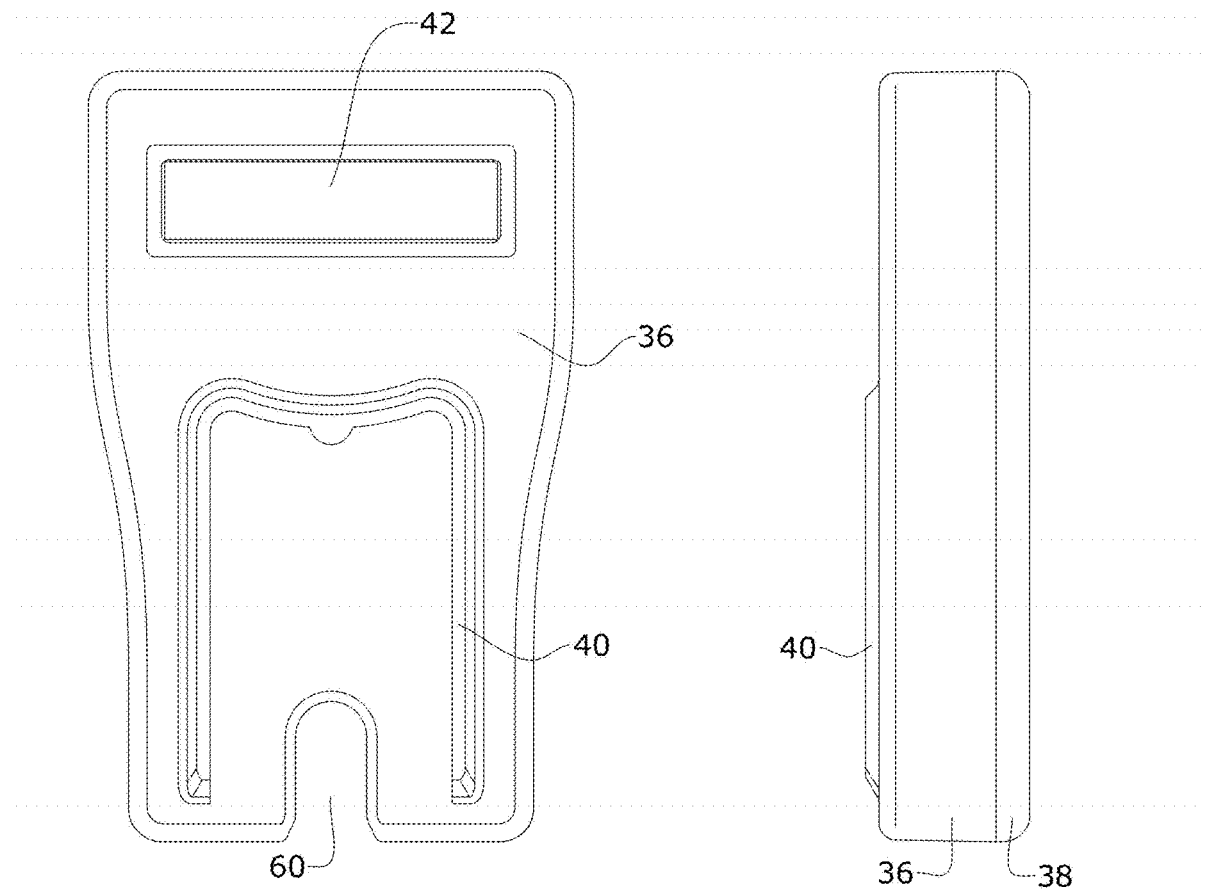

FIG. 11 conceptually illustrates a top view of the second applied usage count reader and display device in some embodiments.

FIG. 12 conceptually illustrates a side view of the second applied usage count reader and display device in some embodiments.

Figures 13, 14:
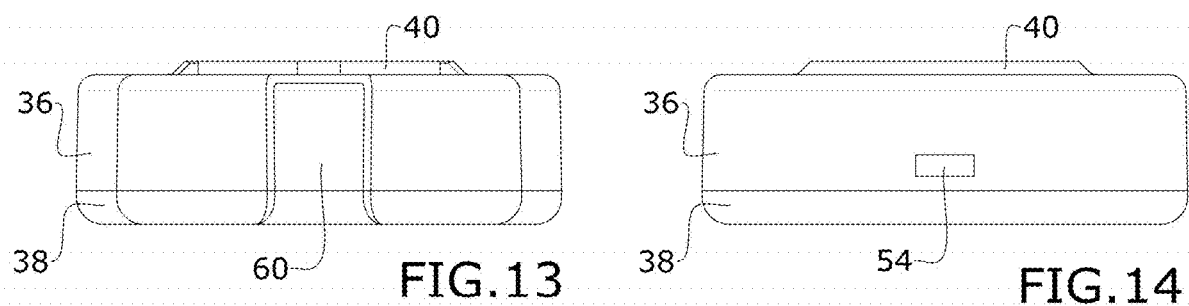

FIG. 13 conceptually illustrates a front view of the second applied usage count reader and display device in some embodiments.

FIG. 14 conceptually illustrates a rear view of the second applied usage count reader and display device in some embodiments.

Figure 15:
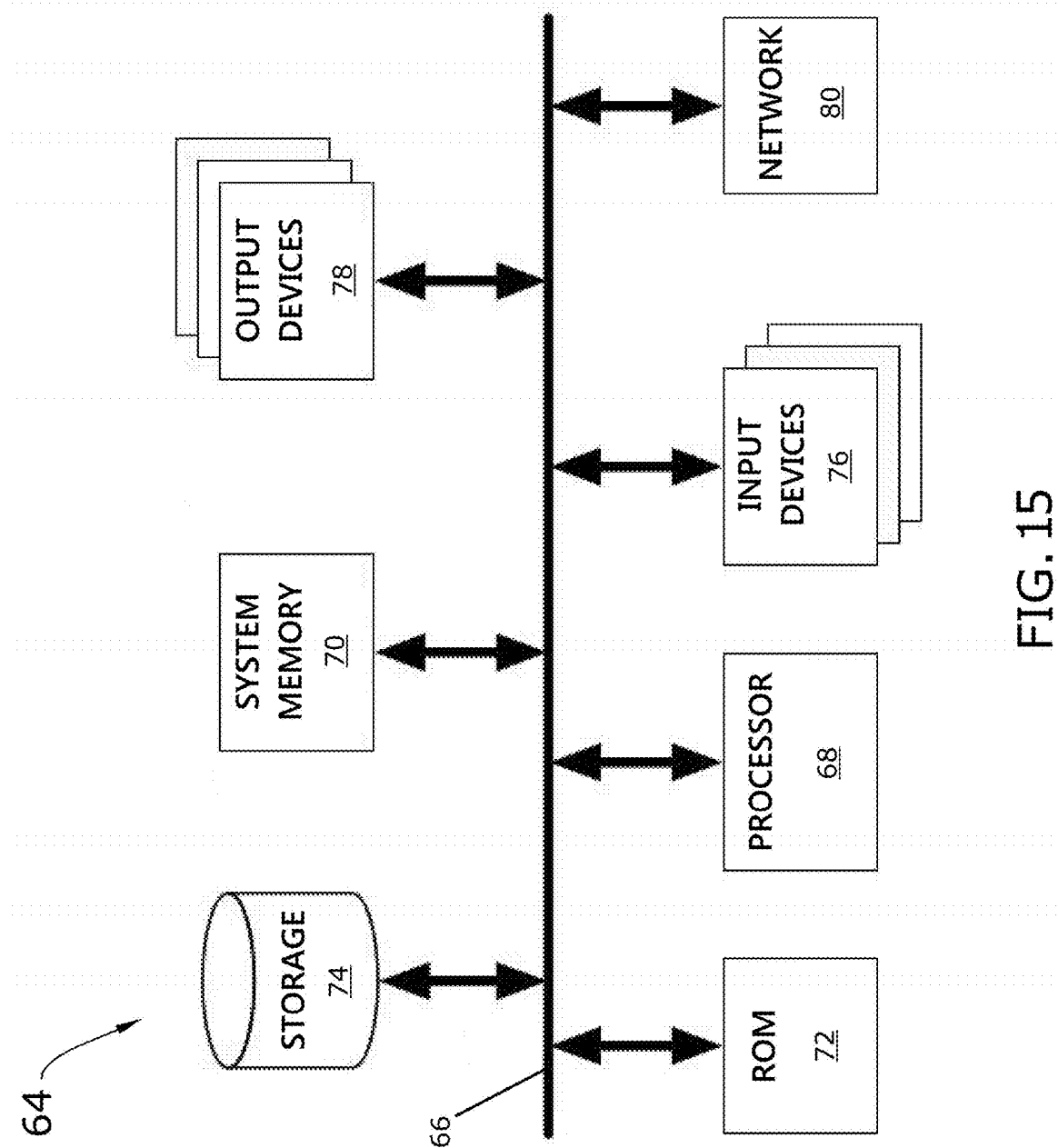

FIG. 15 conceptually illustrates an electronic system with which some embodiments of the invention are implemented.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide an applied usage count reader and display device configured to determine a number of applied uses remaining for a limited-use medical device or instrument used by a surgical or robotic system. In some embodiments, the applied usage count reader and display device reads internally stored data, including the number of applied uses remaining and other pertinent data about the limited-use medical device, as retrieved from the limited-use medical device/instrument without need of the surgical/robotic system. In some embodiments, the internally stored data read by the applied usage count reader and display device comprises data specifying the number of applied uses remaining. In some embodiments, the internally stored data further comprises data specifying a make, a model number, a serial number, a version number, an internal specification, and/or other pertinent data about the limited-use medical tool. In some embodiments, the applied usage count reader and display device is configured for use in writing and/or reprogramming data. In some embodiments, the applied usage count reader and display device is configured for resetting the number of applied uses remaining. For instance, writing or reprogramming data or resetting the number of applied uses remaining for a limited-use medical tool provided for repairing, refurbishing, or remanufacturing.

In some embodiments, the applied usage count reader and display device is a hand-held device. In some embodiments, the applied usage count reader and display device is a portable device. In some embodiments, the applied usage count reader and display device is a mobile device. In some embodiments, the applied usage count reader and display device is an integrated device (integrated with other hardware). In some embodiments, the applied usage count reader and display device is powered by batteries. In some embodiments, the applied usage count reader and display device is powered by AC power. In some embodiments, the applied usage count reader and display device is powered by a non-battery DC power source or other power source.

In some embodiments, the applied usage count reader and display device is a first applied usage count reader and display device that is configured to read internally stored data to determine a number of applied uses remaining for a first type of instrument used in connection with a robotic surgical system. In some embodiments, the first applied usage count reader and display device comprises (i) a housing box comprising a front cover and a back cover, with extending flanges along the front cover to cradle the first type of limited-use medical instrument as it slides in the top of a mounting point of the housing box, (ii) a plurality of surface mounted contacts of a contact printed circuit board (PCB) assembly, where the plurality of surface mounted contacts are configured to align with a plurality of pogo pins embedded into the first type of limited-use medical instrument, (iii) a printed circuit board assembly (PCBA) encapsulated within the housing box and proximate to the plurality of surface mounted contacts, where the PCBA comprises an EEPROM reader and an embedded program (embedded software program or application) to decode data retrieved by the EEPROM reader from an EEPROM memory unit embedded within the first type of limited-use medical instrument, (iv) a power source compartment comprising one of a battery compartment configured to hold batteries and an AC power port and receptacle, (v) a USB port that is configured to connect to an external computing device and/or receive external power, (vi) an optional activation button that is configured to trigger the EEPROM reader to retrieve data from the first type of limited-use medical instrument for decoding by the program running on the PCBA for visual display of the remaining usage data, and (vii) a display screen configured to visually output the remaining usage data, and the other internally stored data as needed, of the first type of limited-use medical instrument. In some embodiment, the display screen comprises an LCD display screen. In some embodiment, the display screen comprises an OLED display screen. In some embodiments, the display screen is flush mounted along the front cover of the housing. In some embodiments, the display screen is angle mounted. In some embodiments, the display screen is mounted to protrude above the front cover of the housing. In some embodiments, the display screen preferrably has a size dimension of 16×2. In some other embodiments, the display screen has a larger size dimension or a smaller size dimension than the preferred size dimension. In some embodiments, the EEPROM reader of the first applied usage count reader and display device is configured to retrieve data for the number of applied uses remaining, and the other internally stored data, from the EEPROM memory unit embedded in the first type of limited-use medical instrument. In some embodiments, the program running on the PCBA then decodes the data and prepares the data for the number of applied uses remaining and any of the other retrieved internally stored data, as needed, in human-readable format for visual output to the display screen.

In some embodiments, the plurality of surface mounted contacts comprises five surface mounted contacts. In some embodiments, the plurality of surface mounted contacts comprises less than five surface mounted contacts. In some embodiments, the plurality of surface mounted contacts comprises a number of surface mounted contacts that is equivalent to a number of pogo pins of the first type of limited-use medical instrument. In some embodiments, two surface mounted contacts in the plurality of surface mounted contacts are utilized to retrieved data from the EEPROM memory unit when the pogo pins of the first type of limited-use medical instrument make contact with the surface mounted contacts.

In some embodiments, the applied usage count reader and display device is a second applied usage count reader and display device that is configured to read internally stored data to determine a number of applied uses remaining for a second type of limited-use medical instrument used in connection with a robotic surgical system. In some embodiments, the second applied usage count reader and display device comprises (i) a housing with a medical instrument shaft cavity, wherein the housing is made by a front cover with an instrument guide and back cover, which are secured together to encapsulate several embedded components, (ii) a magnetic activated sensor (or "reed switch") encapsulated within the housing, (iv) a printed circuit board assembly (PCBA) encapsulated within the housing, (v) a radio-frequency identification (RFID) active reader and antenna, (vi) a power source compartment comprising one of a battery compartment configured to hold batteries as a power source and a power port receptacle configured to accept AC power, (vii) a USB port that is configured to connect to an external computing device and/or receive electricity from an external power source, (viii) an optional activation button, and (ix) a display screen configured to visually output the remaining usage data, and the other internally stored data as needed, for the second type of limited-use medical instrument. In some embodiments, the second type of limited-use medical instrument includes a magnet that is detected by the reed switch (magnetic activated sensor) of the second applied usage count reader and display device which triggers an embedded RFID antenna to energize and transmit a radio signal to energize an RFID tag of the second type of instrument and send data for the number of applied uses remaining, and the other internally stored data, from the second type of instrument to an RFID active reader and antenna of the second applied usage count reader and display device, which decodes the data and displays the number of applied uses remaining and other information from the internally stored data as needed. In some embodiments, the display screen comprises one of an LCD display screen and an OLED display screen. In some embodiments, the display screen is flush mounted along the front cover of the housing. In some embodiments, the display screen is angle mounted. In some embodiments, the display screen is mounted to protrude above the front cover of the housing. The display screen has a preferred size dimension of 16×2. However, in some embodiments, the display screen has a larger size dimension or a smaller size dimension than the preferred size dimension.

As stated above, when a limited-use medical tool is disconnected from the surgical system, it is not possible to determine the information embedded on the memory of the limited-use medical tool, such as the number of uses, or other pertinent data left on the limited-use medical tool. The applied usage count reader and display device that determines a number of applied uses remaining for a limited-use medical device or instrument used by a surgical or robotic system claimed here solves this problem by reading the information embedded on the memory of the limited-use medical tool. This information is important to determine if the limited-use medical tool has any uses left and/or so that it is not discarded by mistake or reprocessed and sent to the operating room with zero (0) uses available. The information is also useful to determine whether to buy new instruments, sell existing instruments, and/or repair used instruments.

Embodiments of the applied usage count reader and display device described in this specification differ from and improve upon currently existing options. In particular, the only way to read the memory on a limited-use medical tool is to connect the limited-use medical tool to a very expensive surgical system in the operating room. Therefore, the only existing way for hospital staff to determine the number of uses left on the limited-use medical tool is connect it to the surgical system in the operating room, and then to physically mark the surface of the limited-use medical tool each time the limited-use medical tool is used. However, this is prone to human error and incorrect markings of the remaining uses can, and do, occur. Also, the physical, staff-made markings can fade, wear off, or become illegible during cleaning and sterilization.

By contrast, the applied usage count reader and display device of the present disclosure allows the hospital staff, repair and/or service agents, resellers, distributors, and others to read the embedded usage information and other internally stored data of the limited-use medical tool without it being connected to an expensive surgical system or even being anywhere near the operating room. As such, the applied usage count reader and display device removes the human element from the determination of uses left on the limited-use medical tool. Specifically, the applied usage count reader and display device allows staff to test the uses and memory on the limited-use medical tool at any time when you are away from the surgical system or operating room. In this way, the applied usage count reader and display device solves the problem of reading the useful remaining applications (or "lives") of the limited-use medical tool before it is sterilized, discarded, or mistakenly reprocessed (based, e.g., on inaccurate surface markings) and sent to the operating room with no uses left. This saves money for hospitals and medical facilities and reduces downtime in the operating room when having to replace an expired limited-use medical tool with one that has remaining usage applications left.

The applied usage count reader and display device of the present disclosure may be comprised of the following elements. This list of possible constituent elements is intended to be exemplary only and it is not intended that this list be used to limit the applied usage count reader and display device of the present application to just these elements. Persons having ordinary skill in the art relevant to the present disclosure may understand there to be equivalent elements that may be substituted within the present disclosure without changing the essential function or operation of the applied usage count reader and display device.

1. Plastic or metallic box (or other material housing, glass, ceramic, etc., or other non-ferrous material for the second applied usage count reader and display device, or other with an embedded magnet activated sensor/reed switch, to allow operation of a reed switch), that acts as a housing of the applied usage count reader and display device, with extending flanges or instrument guide to cradle the limited-use medical tool as it slides in from the top of the mount (cradling the limited-use medical tool is optional since the applied usage count reader and display device is equipped with a magnetic sensor, which can be nearby the limited-use medical tool or instrument without it being cradled and still operate to read the data on the limited-use medical tool when triggered by depressing the activation button). The housing is designed to be water/chemical resistant, thereby allowing the applied usage count reader and display device to be cleaned.
2. A plurality of surface mounted contacts of the first applied usage count reader and display device that align with pogo pins of the first type of limited-use medical tool and/or magnetic activated sensor for the second applied usage count reader and display device configured to detect a magnet of the second type of limited-use medical instrument.
3. A widow and display screen (LCD, OLED, LED, etc.) for the embedded display. The display screen can be a relatively small form factor (e.g., 16×2) or may be larger. The display screen can be flush mounted to the housing or may be angled or protrude outward and above the housing, or take another form, such as a flip up screen that is flush when in a flipped-down mode and protrudes upward at an angle when in a flipped-up mode. Also, the display screen is not a requirement since visual output of data may be configured to display on an external display device via the USB data port or wirelessly or via another display output port that connects to the external display by wired connect and/or wireless connection.
4. An optional activation button on the side of the housing. In some embodiments, the activation button is configured to enable a user to activate the applied usage count reader and display device. In some embodiments, the activation button is an optional element to activate the applied usage count reader and display device. In some embodiments, the activation button is a removable component of the applied usage count reader and display device.
5. A rear door or back cover/panel for installation of batteries or a power receptor/receptacle.
6. Enclosed nearby the five surface mounted contacts is a printed circuit board assembly (PCBA) which includes an EEPROM reader and/or a RFID active reader and antenna.
7. A power supply (e.g., batteries, AC power, etc.) and a data transmission mechanism and port, such as a data port (e.g., USB, Ethernet, powered Ethernet, etc.), wireless data transceiver, WiFi, Bluetooth, NFC, etc. The data transmission mechanism and port are configured in some embodiments for combined power and data. The data transmission mechanism and port enable program editing, program upload, and program download to reprogram, edit, or write as well as to download data, or directly access the PCBA via an external computing device (e.g., a connected laptop), and also to provide power to operate the applied usage count reader and display device. For instance, an embedded program on the applied usage count reader and display device may be configured to read only the number of available uses remaining for a medical instrument, but may be accessed via the data transmission mechanism to edit and save as an updated program on the applied usage count reader and display device to read the number of available uses remaining and all other internally stored data on the medical instrument. In this way, the applied usage count reader and display device is readily adaptable to be used in expansive ways with respect to reading information stored on such robotic system medical instruments.

The various elements of the applied usage count reader and display device of the present disclosure may be related in the following exemplary fashion. It is not intended to limit the scope or nature of the relationships between the various elements and the following examples are presented as illustrative examples only. The extending flanges or instrument guide allow for easy alignment of the limited-use medical tool to be read if using the EEPROM reader or for the magnet to be detected if using the magnet activated sensor (reed switch). The surface mounted contacts of the first applied usage count reader and display device allow for contact to the pogo pins of the first type of limited-use medical tool, thereby allowing data to be read from the EEPROM. On the other hand, the second type of limited-use medical instrument may include an RFID tag such that the magnetic sensor of the second applied usage count reader and display device can trigger the RFID active reader to power on to energize the RFID tag to transmit its data for the second applied usage count reader and display device to receive and decode. The activation button is optional, but when present, is designed for human interaction along the side of the housing to trigger activation of the applied usage count reader and display device to read the data from the limited-use medical instrument (e.g., surface mounted contacts to pogo pins or by magnetic activated sensor triggering the RFID signal to energize the RFID tag in the second type of limited-use medical instrument and receive the data by the RFID active reader). The batteries or power receptor supply power to the PCBA, the reader, and the display, and any other power consuming component. Batteries/power receptor or the PCBA may be accessed through the rear door/back cover. The PCBA will record and decipher the information read from the EEPROM reader or the RFID active reader and display the results on the display screen. Data from the PCBA may be downloaded or the PCBA may be accessed via USB port or connected to an external computer or memory device. The data may be download to a spreadsheet or other data repository, may trigger a third party cloud application service to perform corresponding action(s) (e.g., such as by IFTTT.com sending email, SMS, etc., with count as scanned).

The applied usage count reader and display device of the present disclosure generally works by inserting the limited-use medical tool into the cradle of the box. Upon inserting the limited-use medical tool, the magnetic sensor is triggered or a user depresses the activation button, so that the applied usage count reader and display device is powered up and the information on the EEPROM or RFID tag of the limited-use medical tool is read by the EEPROM reader or RFID active reader of the applied usage count reader and display device. This information will be extrapolated and deciphered by the PCBA, which is pre-programmed to extrapolate and decipher the information, so that the deciphered data, such as number of remaining usages (lives left) and/or lot and serial number, and/or reference number, etc., on the limited-use medical tool will be displayed on the display screen of the applied usage count reader and display device. This data may also be stored on the applied usage count reader and display device or downloaded via USB port or connected to an external computer or memory device.

To make the applied usage count reader and display device of the present disclosure, a person may assemble the box with integrated flanges (housing of the applied usage count reader and display device) to the display screen and the flush mounted contact pins and/or magnetic sensor. Continue with assembly of the PCBA along with the EEPROM reader or the RFID antenna, RFID active reader, and reed switch (usually assembled to the PCBA) and USB port, inside the box, as well as assembly of the battery holder and install the batteries or assemble the power connector.

In some embodiments, the applied usage count reader and display device can be made into two separate units: one unit to read, decipher, and display information only from the EEPROM of a limited-use medical tool, and another unit to read, decipher, and display information only from with RFID tag of a limited-use medical tool. The applied usage count reader and display device could be integrated into a stand alone computer which is programmed to read, decipher, and display the information gathered with a separate EEPROM reader or a separate RFID active reader connected via a USB or similar connection to process and display the information.

To use the applied usage count reader and display device of the present disclosure, for a limited-use medical tool with the EEPROM, a person simply needs to insert the limited-use medical tool into the applied usage count reader and display device. The applied usage count reader and display device will automatically turn on and read, decipher, and record the information from the limited-use medical tool and display the read information on the display screen. Furthermore, the applied usage count reader and display device of some embodiments is configured for use in writing and/or reprogramming data or for resetting the number of applied uses remaining for a limited-use medical instrument. For instance, service personnel may use the applied usage count reader and display device to write data or to reprogram in order to apply data or reset the number of applied uses remaining for a limited-use medical instrument.

For a limited-use medical tool with the RFID tag, a person would use the applied usage count reader and display device by placing the limited-use medical tool nearby the applied usage count reader and display device (preferably cradled within the instrument guide) and (optionally and manually) depress the activation button or (automatically by detection of a magnet) activate the applied usage count reader and display device via the magnet activated sensor. The applied usage count reader and display device will automatically turn on and read, decipher, and record the information from the limited-use medical tool and display the read information on the display screen.

By way of example, FIG. 1 conceptually illustrates a perspective view of a limited-use robotic instrument engaged with an applied usage count reader and display device in some embodiments. Shown in this figure is a first type of applied usage count reader and display device (or "first applied usage count reader and display device", also known as the "Si applied usage count reader and display device") that works in connection with a first type of robotic instrument 32. The first applied usage count reader and display device comprises a front cover 10, a back cover 12, a display screen 16, an activation button 28, and a universal serial bus (USB) data cable 34. To use the first applied usage count reader and display device to read the number of available uses remaining, and other internally stored data, on the robotic instrument 32, the robotic instrument 32 needs to be properly connected to the first applied usage count reader and display device.

The USB data cable 34 may be configured to provide a data transmission mechanism or to supply power and provide a data transmission mechanism. When connected to another computing device, the USB data cable 34 may provide access to an embedded printed circuit board assembly (PCBA) of the first applied usage count reader and display device and/or embedded software or control modules on the PCBA to rewrite or reprogram as needed. The USB data cable 34 also allows for data to be uploaded onto (transmitted to) or downloaded from (retrieved) the first applied usage count reader and display device when connected to the other computing device. While noted to be a USB cable in this example, a person of ordinary skill in the relevant art would appreciate the other hard wire or wireless data transfer mechanisms could be used instead, such as, without limitation, an Ethernet cable, a powered Ethernet cable, WiFi, Bluetooth, NFC, etc.

By way of example, FIG. 2 conceptually illustrates a perspective view of the first applied usage count reader and display device of FIG. 1, but without the robotic instrument 32 connected. Specifically as shown in this figure, a guide flange 14 is demonstrated and the location of the first applied usage count reader and display device at which the robotic instrument 32 connects includes a plurality of surface mounted contacts that are configured to align with pogo pins on the bottom side of the robotic instrument 32 when properly connected. A proper connection is established when the surface mounted contacts of the first applied usage count reader and display device contact the pogo pins of the robotic instrument 32. After establishing a proper connection between the pogo pins of the robotic instrument 32 and the plurality of surface mounted contacts of the first applied usage count reader and display device, a person using the first applied usage count reader and display device (or simply, the "user") can press the activation button 28 to have the first applied usage count reader and display device read the number of available uses remaining on the robotic instrument 32, as well as the other internally stored data. When the number of available uses is ascertained, the first applied usage count reader and display device visually outputs the number onto the display screen 16 for the user to view. In some embodiments, other information is visually output, as needed, based on the other internally stored data retrieved from the robotic instrument 32. For example, the make of the robotic instrument 32, the model number, serial number, and/or version of the robotic instrument 32, etc.

By way of another example, FIG. 3 conceptually illustrates an exploded view of the first applied usage count reader and display device in some embodiments. As shown in this figure, the first applied usage count reader and display device includes the components and elements noted above, by reference to FIGS. 1 and 2, namely, the front cover 10, the back cover 12, the guide flange 14, the display screen 16, the activation button 28, and the USB data cable 34. Additionally, the guide flange 14 is configured to hold the robotic instrument 32 in place on top of the first applied usage count reader and display device so that the pogo pins of the robotic instrument 32 make contact with the surface mounted contacts.

However, unlike the views of the first applied usage count reader and display device shown in FIGS. 1 and 2, the first applied usage count reader and display device shown in FIG. 3 includes additional elements and components, and provides more detail about the various elements and components. Specifically, the front cover 10 is shown in this figure with cut outs, namely, a universal serial bus ("USB") data port 30 to which the USB data cable 34 connects and another cut out in which the activation button 28 fits. The remaining additional elements and components of the first applied usage count reader and display device shown in this figure are embedded elements and components. The embedded elements and components of the first applied usage count reader and display device comprise a main printed circuit board 18 ("main PCB 18"), a battery holder 20, a plurality of batteries 22 that provides power to both the display screen 16 and the main printed circuit board 18 of the first applied usage count reader and display device, a contact printed circuit board 24 ("contact PCB 24"), a contact retainer 26 configured to secure the contact PCB 24 in place, and a plurality of screws to secure the back cover 12 to the front cover 10 and to secure the embedded components and elements within the first applied usage count reader and display device. Also, the display screen 16 is only partially embedded within the first applied usage count reader and display device. Specifically, a screen surface of the display screen 16 is flush mounted for viewing from the outside of the first applied usage count reader and display device while a display screen circuit board is assembled to connect to the main printed circuit board 18.

In some embodiments, the contact PCB 24 comprises a plurality of surface mounted contacts that align with pogo pins embedded into the robotic instrument 32 when the robotic instrument 32 is mounted to the first applied usage count reader and display device and held in place by the guide flange 14. In some embodiments, the robotic instrument 32 includes an EEPROM memory unit that stores data for the available number of uses remaining for the robotic instrument 32. In some embodiments, the contact PCB 24 provides function as an EEPROM reader when the surface mounted contacts are in contact with the pogo pins of the robotic instrument 32. In some embodiments, the contact PCB 24 provides the data retrieved from the EEPROM memory unit of the robotic instrument 32 to a program running on the main printed circuit board 18, where the program is configured to decode the data and determine the number of remaining uses of the robotic instrument 32

While not shown in this figure, the first applied usage count reader and display device also includes internal wiring. Specifically, power wiring is included from the battery holder 20 and the plurality of batteries 22 to the main printed circuit board 18 and the display screen circuit board connected to the display screen 16. Other wiring provides contact activation-specifically, wiring from the contact PCB 24 to the main printed circuit board 18 ensures that when the activation button 28 is pressed and the pogo pins of the robotic instrument 32 are aligned with the plurality of surface mounted contacts of the contact PCB 24. This allows for an embedded program to carry out a read or scan operation in connection with the robotic instrument 32. And the read/scan operation is performed to read the number of remaining available uses of the robotic instrument 32, and the other internally stored data, without requiring the actual robot to perform the read/scan operation, thereby saving time and allowing for better planning management.

Turning now to a number of other views of the first applied usage count reader and display device, FIG. 4 conceptually illustrates a top view of the first applied usage count reader and display device, which shows the front cover 10, the guide flange 14, the visible surface portion of the display screen 16, the activation button 28 along the right side of the first applied usage count reader and display device, and a plurality of surface mounted contacts 62. The plurality of surface mounted contacts 62 align with pogo pins of the robotic instrument 32 when the robotic instrument 32 is mounted to the first applied usage count reader and display device and held in place by the guide flange 14.

Specifically, the plurality of surface mounted contacts 62 are from the contact PCB 24, which is embedded within the first applied usage count reader and display device. In the top view orientation shown in this figure, the plurality of surface mounted contacts 62 are visibly exposed within pogo pin guide channels of the front cover 10. In some embodiments, the guide flange 14 constrains mounting of the robotic instrument 32 such that the pogo pins of the robotic instrument 32 are properly aligned within the pogo pin guide channels of the front cover 10. In this way, proper contact between the mounted robotic instrument 32 and the embedded contact PCB 24 is ensured, thereby allowing the first applied usage count reader and display device to read the number of available uses remaining, and the other internally stored data, for the robotic instrument 32.

Also, while the activation button 28 in this view is shown along the right side of the first applied usage count reader and display device, a person of ordinary skill in the relevant art would appreciate that different design considerations could be applied, such that the activation button 28 is positioned along the left side of the first applied usage count reader and display device, along the top or bottom sides of the first applied usage count reader and display device, on top or under the bottom of the first applied usage count reader and display device, or at a different relative position along the right side (or any other side) of the first applied usage count reader and display device.

In FIG. 5, a side view of the first applied usage count reader and display device is shown. In this view, the right side of the first applied usage count reader and display device is demonstrated with the front cover 10, the back cover 12, the guide flange 14, and the activation button 28 visible. By way of another view, FIG. 6 conceptually illustrates a front view of the first applied usage count reader and display device with the front cover 10, the back cover 12, the guide flange 14, and the activation button 28 of the first applied usage count reader and display device visible. Finally, FIG. 7 conceptually illustrates a rear view of the first applied usage count reader and display device in some embodiments. Shown in this rear view are the front cover 10, the back cover 12, the guide flange 14, the activation button 28, and the USB data port 30 into which a USB data cable 34 (not shown in this figure) can connect.

Now turning to another embodiment of the applied usage count reader and display device. By way of example, FIG. 8 conceptually illustrates a perspective view of a limited-use robotic instrument engaged with an applied usage count reader and display device in some embodiments. A second type of applied usage count reader and display device (or "second applied usage count reader and display device", also known as the "Xi applied usage count reader and display device") is shown in this figure. The second applied usage count reader and display device works in connection with a second type of robotic instrument 56. The second applied usage count reader and display device comprises a front cover 36, a back cover 38, an instrument guide 40, a display screen 42, a universal serial bus ("USB") data cable 58, and an opening for an instrument shaft 60 of the robotic instrument 56.

To use the second applied usage count reader and display device to read the number of available uses remaining, and the other internally stored data, for the robotic instrument 56, the robotic instrument 56 needs to be properly mounted to the second applied usage count reader and display device, or at least nearby the second applied usage count reader and display device. For proper mounting, the instrument guide 40 and the opening for the instrument shaft 60 constrain the mounting of the robotic instrument 56 to ensure a proper mount to the second applied usage count reader and display device. Furthermore, unlike the first applied usage count reader and display device with the activation button 28, the second applied usage count reader and display device does not include an activation button. (Note, in some embodiments, the second applied usage count reader and display device can optionally include an activation button, even though not show in this figure.) Instead of an activation button, a magnetic activated sensor is embedded within the second applied usage count reader and display device. In some embodiments, the magnetic activated sensor is a reed switch that is configured to activate the second applied usage count reader and display device when the robotic instrument 56 is nearby, or preferably, mounted properly to the second applied usage count reader and display device within an area conforming to the instrument guide 40. The strength of one or more magnet(s) in the robotic instrument 56 as well as the sensitivity of the magnetic activated sensor and possible other factors will determine a nearby distance from which the robotic instrument 56 can be away from the second applied usage count reader and display device and still operate as intended. However, when properly mounted, the magnet(s) of the robotic instrument 56 virtually come into contact with the front cover 36 of the second applied usage count reader and display device and the reed switch is able to detect the magnet(s) of the properly mounted robotic instrument 56. The magnetic activated sensor (reed switch) is further described below, by reference to FIG. 10.

The USB data cable 58 may be utilized for data transmission and/or for supplying power to operate the second applied usage count reader and display device or recharge the batteries. In some embodiments, utilizing the USB data cable 58 for data transmission provides access to an embedded printed circuit board assembly (PCBA) of the second applied usage count reader and display device and/or embedded software or control modules on the PCBA to rewrite or reprogram as needed. Similarly, data to be uploaded to or downloaded from the second applied usage count reader and display device when the USB data cable 58 connects the second applied usage count reader and display device to another computing device. Although shown and described as a USB cable, other wired and wireless data communication and transmission mechanisms are anticipated and supported, such as Ethernet cables, powered Ethernet cables, WiFi, Bluetooth, NFC, etc.

By way of example, FIG. 9 conceptually illustrates a perspective view of the second applied usage count reader and display device of FIG. 8, but without the robotic instrument 56 mounted and without the USB data cable 58.

By way of another example, FIG. 10 conceptually illustrates an exploded view of the second applied usage count reader and display device in some embodiments. As shown in this figure, the second applied usage count reader and display device includes the front cover 36, the back cover 38, the instrument guide 40, the display screen 42, the USB data cable 58, and the opening for the instrument shaft 60 of the robotic instrument 56. Additionally, a universal serial bus ("USB") data port 54 is shown along a rear side of the front cover 36. The USB data cable 58 connects to the USB data port 54 for data communication to and from the second applied usage count reader and display device. Additionally, the second applied usage count reader and display device comprises several embedded components including a main printed circuit board (PCB) 44 to which the display screen 42 is assembled, a reed switch 46, a radio frequency identification (RFID) reader and antenna 48, a battery holder 50, a plurality of batteries 52, and a plurality of screws that secure the embedded components and secure the back cover 38 to the front cover 36.

In some embodiments, the second applied usage count reader and display device reads the number of available uses, and the other internally stored data, of a limited-use robotic instrument that includes a magnet. In some embodiments, the reed switch 46 is a magnetic activated sensor with normally open contacts which close and connect when a magnet is nearby. Thus, when the robotic instrument 56 is positioned within the instrument guide 40 on the second applied usage count reader and display device, the reed switch 46 is triggered and electricity flows to the RFID reader and antenna 48 which sends radio signals that energize a corresponding antenna in the robotic instrument 56. This results in the robotic instrument 56 reading the stored data and sending out as radio signals captured back at the RFID reader and antenna 48. The data is then processed by a program running on the main PCB 44 to decode the information and determine the number of available uses remaining on the robotic instrument 56, as well as any of the other internally stored data as needed (specified by embedded software on the second applied usage count reader and display device).

Turning now some other views of the second applied usage count reader and display device, FIG. 11 conceptually illustrates a top view of the second applied usage count reader and display device. This view demonstrates where the robotic instrument 56 aligns properly within the instrument guide 40 such that the shaft of the robotic instrument 56 protrudes down through the opening for the instrument shaft 60. This view also shows the display screen 42 mounted at a cut out/cavity of the front cover 36. FIG. 12 conceptually illustrates a side view of the second applied usage count reader and display device in some embodiments. From this side view, the instrument guide 40 is visible slightly above the front cover 36 which attaches to the back cover 38 of the second applied usage count reader and display device. Unlike the activation button 28 included with the first applied usage count reader and display device described above by reference to FIGS. 1-7, the second applied usage count reader and display device does not include an activation button, relying instead on the reed switch 46 to activate when a magnet of the robotic instrument 56 is detected. Now from another perspective, FIG. 13 conceptually illustrates a front view of the second applied usage count reader and display device in some embodiments. Show in this view are the front cover 36, the back cover 38, the instrument guide 40, and the instrument shaft opening 60. From the opposite view, FIG. 14 conceptually illustrates a rear view of the second applied usage count reader and display device showing the front cover 36, the back cover 38, the instrument guide 40, and the USB data port 54 into which a user may plug the USB data cable 58 to connect the second applied usage count reader and display device to a power source and/or an external computing device.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "program", "application", "embedded software", "embedded program", and/or "embedded application" (referred to below as "software") are meant to include firmware residing in read-only memory or applications stored in magnetic storage of printed circuit board (PCB) assemblies, which can be read into memory for processing by a processor, such as the processor of the main or contact PCB, or the processor of a traditional computing device (such as an externally-connected computing device such as a desktop or laptop computer, single board computer, tablet, etc.). Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

FIG. 15 conceptually illustrates an electronic system 64 with which some embodiments of the invention are implemented. The electronic system 64 may be the first applied usage count reader and display device, the second applied usage count reader and display device, another applied usage count reader and display device, an external computing device communicably connected to the applied usage count reader and display device, or any other sort of electronic device. Such an electronic system includes various types of computer readable media and interfaces for various other types of computer readable media. Electronic system 64 includes a bus 66, processing unit(s) 68, a system memory 70, a read-only memory 72, a permanent storage device 74, input devices 76, output devices 78, and a network 80.

The bus 66 collectively represents all system, peripheral, and chipset buses that communicatively connect the numerous internal devices of the electronic system 64. For instance, the bus 66 communicatively connects the processing unit(s) 68 with the read-only memory 72, the system memory 70, and the permanent storage device 74.

From these various memory units, the processing unit(s) 68 retrieves instructions to execute and data to process in order to execute the processes of the invention. For instance, the processing unit(s) 68 may retrieve machine code of the program utilized to decode the data retrieved from the robotic instrument and display the number of available uses remaining, and the other internally stored data, for the limited-use robotic instrument. The processing unit(s) may be a single processor or a multi-core processor in different embodiments.

The read-only-memory (ROM) 72 stores static data and instructions that are needed by the processing unit(s) 68 and other modules, such as the reed switch and/or other magnet activated sensor (not shown in this figure), of the electronic system 64. The permanent storage device 74, on the other hand, is a read-and-write memory device. This device is a non-volatile memory unit that stores instructions and data even when the electronic system 64 is off. Some embodiments of the invention use a mass-storage device (such as a magnetic or optical disk and its corresponding disk drive) as the permanent storage device 74.

Other embodiments use a removable storage device (such as an insertable flash memory module) as the permanent storage device 74. Like the permanent storage device 74, the system memory 70 is a read-and-write memory device. However, unlike storage device 74, the system memory 70 is a volatile read-and-write memory, such as a random access memory. The system memory 70 stores some of the instructions and data that the processor needs at runtime. In some embodiments, the invention's processes are stored in the system memory 70 (embedded), the permanent storage device 74, and/or the read-only memory 72. From these various memory units, the processing unit(s) 68 retrieves instructions to execute and data to process in order to execute the processes of some embodiments.

The bus 66 also connects to the input and output devices 76 and 78. The input devices enable the user to communicate information and select commands to the electronic system 64. The input devices 76 include USB and/or wirelessly connected devices with alphanumeric keyboards or virtual keyboard screens and pointing devices/virtual pointing device (also called "cursor control devices"). The output devices 78 display images generated by the electronic system 64. The output devices 78 include display devices, such as a 16×2 LCD display screen, or other larger/smaller display screens, such as organic light emitting diode (OLED) display screens. Some embodiments include devices such as a touchscreen that functions as both input and output devices. These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Finally, as shown in FIG. 15, bus 66 also couples electronic system 64 to a network 80 through a network adapter (not shown). In this manner, the electronic system 64 can be a part of a network of computing devices and network systems (such as a local area network ("LAN"), a wide area network ("WAN"), or an intranet), or a network of networks (such as the Internet).

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. For instance, in some embodiments, the applied usage count reader and display device is configured to write to and/or reprogram a limited-use medical tool or instrument. Thus, one of ordinary skill in the art would understand that the invention is not to be limited by the foregoing illustrative details, but rather is to be defined by the appended claims.

We claim:

1. An applied usage count reader device comprising:
   a radio frequency identification (RFID) reader and antenna that is configured to emit radio signals to energize an RFID tag of a limited-use medical instrument that (i) stores pertinent data comprising a number of available uses and (ii) is configured for use in a robotic surgical system when the number of available uses in the pertinent data is greater than zero, wherein the limited-use medical instrument is configured to change the number of available uses in the pertinent data each time the limited-use medical instrument is used in the robotic surgical system;
   a printed circuit board assembly (PCBA) that is communicably connected to the RFID reader and antenna, wherein the PCBA is configured to (i) receive the pertinent data from the limited-use medical instrument when the radio signals transmitted by the RFID reader and antenna energize the RFID tag of the limited-use medical instrument and (ii) read the received pertinent data to determine the number of available uses remaining for the limited-use medical instrument without changing the number of available uses in the pertinent data stored on the limited-use medical instrument;
   a plurality of exterior covers comprising a front cover and a back cover that is secured to the front cover, wherein the plurality of exterior covers encapsulates the PCBA and the RFID reader and antenna within a physical housing box that is physically separate from the limited-use medical instrument and the robotic surgical system; and
   a power source that is configured to provide electrical current to power the RFID reader and antenna, and the PCBA.

2. The applied usage count reader device of claim 1 further comprising:
   a universal serial bus (USB) port that is configured to access data and receive external power as the power source; and
   a power receptor that is configured to receive power via the USB port.

3. The applied usage count reader device of claim 2 further comprising a battery compartment that is encapsulated within the physical housing box and is configured to hold a plurality of batteries that provide electrical current to power the RFID reader and antenna and the PCBA, wherein the batteries are charged by the power received from the power received via the USB port.

4. The applied usage count reader device of claim 1, wherein the pertinent data further comprises other internally stored data about the limited-use medical instrument.

5. The applied usage count reader device of claim 4 further comprising a display screen that is mounted on the physical housing box and exposed along the front cover, wherein the display screen is configured to visually output the number of available uses remaining for the limited-use medical instrument after the PCBA determines the number of available uses by reading the received pertinent data, wherein the display screen is further configured to visually output the other internally stored data about the limited-use medical instrument.

6. The applied usage count reader device of claim 5, wherein the other internally stored data about the limited-use medical instrument comprises a make of the limited-use medical instrument, a model number of the limited-use medical instrument, a serial number of the limited-use medical instrument, a version number of the limited-use medical instrument, and an internal specification of the limited-use medical instrument.

7. The applied usage count reader device of claim 1, wherein the limited-use medical instrument comprises a second type of limited-use medical instrument.

8. The applied usage count reader device of claim 7, wherein the front cover comprises an instrument guide configured for placement of the second type of limited-use medical instrument.

9. The applied usage count reader device of claim 8, wherein the instrument guide is configured to cradle the second type of limited-use medical instrument.

10. The applied usage count reader device of claim 1, wherein the RFID reader and antenna is further configured to receive the pertinent data via radio signal transmission from the limited-use medical tool, wherein the received pertinent data comprises encoded data with the number of available uses remaining for the limited-use medical instrument and other data about the limited-use medical instrument.

11. The applied usage count reader device of claim 1, wherein the RFID reader and antenna is magnetically activated upon movement of the applied usage count reader device nearby the limited-use medical instrument.

12. The applied usage count reader device of claim 11, wherein the RFID reader and antenna is configured to emit radio signals when movement of the applied usage count reader device is sufficiently nearby to detect the limited-use medical instrument.

* * * * *